United States Patent [19]

Montgomery et al.

[11] 4,357,324

[45] Nov. 2, 1982

[54] PRODRUG DERIVATIVES OF 9β-D-ARABINOFURANOSYL-2-FLUOROADENINE

[75] Inventors: John A. Montgomery; Anita T. Shortnacy, both of Birmingham, Ala.

[73] Assignee: The United States of America as represented by the Department of health and Human Services, Washington, D.C.

[21] Appl. No.: 237,617

[22] Filed: Feb. 24, 1981

[51] Int. Cl.$^3$ .................... A61K 31/70; C07H 19/18; C07H 19/20

[52] U.S. Cl. .................... 424/180; 536/26; 536/27

[58] Field of Search .................... 536/26, 27; 424/180

[56] References Cited

U.S. PATENT DOCUMENTS

| | | | |
|---|---|---|---|
| 3,703,507 | 11/1972 | Haskell et al. | 536/27 |
| 4,093,714 | 6/1978 | Tolman et al. | 536/27 |
| 4,123,609 | 10/1978 | Behnke et al. | 536/26 |
| 4,136,175 | 1/1979 | Rideout et al. | 536/27 |
| 4,188,378 | 2/1980 | Montgomery | 536/26 |
| 4,210,745 | 7/1980 | Montgomery | 536/26 |

OTHER PUBLICATIONS

Repta et al., "Jour. Phar. Science", 64 pp. 392–396, 1975.

Primary Examiner—Johnnie R. Brown
Attorney, Agent, or Firm—John S. Roberts, Jr.

[57] ABSTRACT

The 5'-formate and the 5'-phosphate derivatives of 9-β-D-arabinofuranosyl-2-fluoroadenine have been prepared as prodrug forms of the anti-cancer agent 9-β-D-arabinofuranosyl-2-fluoroadenine, known as F-ara-A. These derivatives are quite water soluble whereas F-ara-A itself is sparingly soluble in water or in any organic solvents. Delivery of these prodrug forms to mice with L1210 leukemia results in the formation of higher levels of the triphosphate of F-ara-A, the active form of the drug, in the target L1210 leukemia cells. These prodrug forms are much more active chemotherapeutically than 9-β-D-arabinofuranosyladenine, known as ara-A, and equivalent in activity to the combination of ara-A and 2'-deoxycoformycin, known as 2'-dCF, an effective in vivo inhibitor of adenosine deaminase, a ubiquitous enzyme that destroys ara-A in vivo.

7 Claims, 3 Drawing Figures

PRODRUG DERIVATIVES OF 9β-D-ARABINOFURANOSYL-2-FLUOROADENINE

The invention described herein was made in the course of work under a grant or award from the Department of Health and Human Services.

SUMMARY AND DETAILED DESCRIPTION

This invention relates to preparation and utilization in the treatment of leukemia L1210 in mice of new compounds that serve as prodrug forms of the anticancer agent 9-β-D-arabinofuranosyl-2-fluoroadenine, known as F-ara-A. These compounds, the 5'-formate and the 5'-phosphate (F-ara-AMP) of F-ara-A, are water-soluble, chemotherapeutically effective forms of the drug that are converted to the parent drug in vivo. The parent drug is phosphorylated in the target L1210 Leukemia to the triphosphate which causes cell death and, hence, therapeutic activity against the disease. The data in Table I clearly show that the levels of F-ara-ATP in L1210 resulting from near equimolar doses of F-ara, its 5'-formate, F-ara-AMP, and ara-A Plus 2'-dCF are significantly higher from the prodrug forms of F-ara-A than from F-ara-A itself which in turn results in higher levels of the triphosphate than ara-A+2'dCF. These higher levels of the active agent that last for longer periods of time allow effective treatment with these drugs given once a day for nine days (see FIGS. 1, 2 and 3). In contrast, ara-A on its optimal schedule-every 3 hours for 24 hours-is not very effective and even given with 2'-dCF is no better than the prodrug forms of F-ara-A. Thus the properties of these prodrugs will allow them to be used effectively given intravenously once a day as opposed to a constant infusion of a two-drug combination, the second component of which has clear but not completely defined toxicity.

TABLE I

| Treatment | | | Nanomoles of |
|---|---|---|---|
| Agent | Dose (mmole/kg) | Time After Treatment | Triphosphate per gm L1210 cells |
| F-ara-A | 1.4 | 3 | 220 |
|  | 0.5 | 3 | 160 |
| F-ara-A5'-formate | 1.2 | 3 | 400 |
|  | 0.6 | 3 | 125 |
| F-are-AMP | 0.7 | 2 | 220 |
| are-AMP (+2'dCF) | 0.6 | 2 | 110 |
|  |  | 3 | 69 |

For use as anti-cancer agents, the prodrug of this invention or their salts may be given parenterally (in an injectable solution), orally (tablets or capsules), used as a suppository, applied as an ophthalmic solution, or applied topically as an ointment, cream, powder, etc., as a pharmaceutical preparation in accordance with known medical or veterinarial practice. The preferred oral dosage is administered at a dosage of about 10 to 250 mg/kg of mammal body weight (i.e. mice, rats). A controlling dosage of not greater than half the LD 50 is maintained and required.

PRIOR ART STATEMENT

1. U.S. Pat. No. 3,703,507 Haskell/Watson, shows the 9-(Beta-d-arabinofuranosyl) adenine, 5' phosphate.

2. Repta, et al., *J. Pharm. Sci.*, 64 392 (1975) This article teaches the 5' formate of the basic compound F-ara-A.

3. U.S. Pat. No. 4,093,714 Tolman, et al., teaches the 5' phosphorylated 9-β-D-arabinofuranoside.

4. U.S. Pat. No. 4,136,175 Rideout (Burroughs Wellcome Co.) and U.S. Pat. No. 4,123,609 Behnke (Warner-Lambert Co.) both disclose 9-β-D-arabinofuranosyl adenine 5'-phosphate.

TABLE II

Comparison of Activity of 5-Formyl-2-F-ara-A and 2'dCF Plus Ara-A Against L1210

Treatment: IP; QD 1-9 Days*

| $10^5$ IP L1210/0 | Dosage (MG/KG/Dose) | Median Lifespan, Days | % ILS (Cures) |
|---|---|---|---|
| Control (untreated) |  | 9 | — |
| 5-Formyl-2-F-ara-A | 150 | 25 | 177 (3/10) |
| 2'dCF + ara-A | 0.25 + 150 | 13.5 | 50 |
| 2'dCF + ara-AMP | 0.25 + 315 | 13.5 | 50 |

*2'dCF Given 30 Minutes Before ara-A

TABLE III

Activity of ara-A Plus 2'dCF Against L1210/0 Leukemia

Treatment: IP

| $10^5$ IP L1210/0 | Dosage (MG/KG/Dose) | Median Lifespan, Days | % ILS (Cures) |
|---|---|---|---|
| Control (Untreated) |  | 9 | — |
| Ara-A + 2'dCF | 200 + 0.25 | 14 | 55 |
| ara-A + 2'dCF | 54 + 0.2 | 22 | 144 (3/10) |

TABLE IV

Comparison of 2-Fluoro-Ara-AMP and 2'dCF Plus Ara-A Against L1210 Leukemia $10^5$ L1210 Cell IP

| Compound | Dosage mg/kg/day | Schedule | Lifespan Days | % ILS (Cures) |
|---|---|---|---|---|
| Control (untreated) |  |  | 8 |  |
| 2-Fluoro-ara-AMP | 219 | qd 1-9 | 18 | 125(3/10) |
| Ara-AMP | 375 | q3h,days 1,5,9 | 13 | 62 |
| Ara-AMP + 2'dCf | 125 + 0.05 | q3h,days 1,5,9 | 22.5 | 181(4/10) |

Preparation of Prodrug Forms of 9-β-D-arabinofuranosyl-2-fluoroadenine

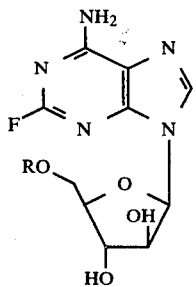

The 5'-formyl derivative (R=CHO) of F-ara-A was prepared by the reaction for F-ara-A with cold 98% formic acid. It was isolated by acetone extraction followed by reverse-phase high-pressure liquid chromatography on a $C_{18}$ using water-acetonitrile as eluant.

The 5'-phosphate (R=H$_2$PO$_3$—) of F-ara-A was prepared by the reaction of F-ara-A with phosphorous oxychloride in an alkyl phosphate followed by hydrolysis in water. The product was purified by adsorption on and elution from a mixture of charcoal and Celite.

The Antitumor Activity

Figure 1:
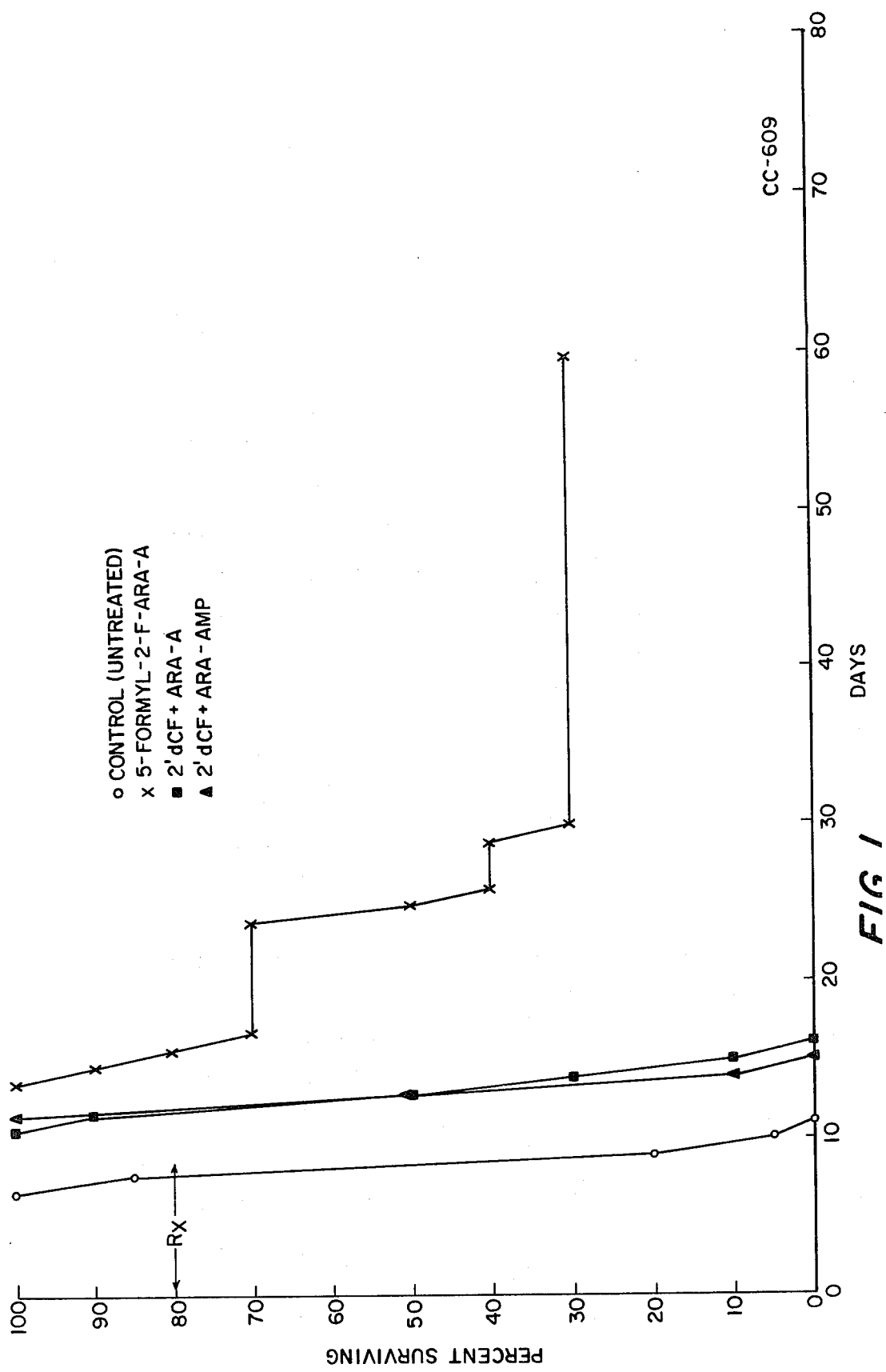
FIG. 1 shows the comparison of activity of 5-formyl-2-F-ara-A and 2'-dCF plus ara-A against L1210/0 Leukemia as further explained in Table II.
Figure 2:
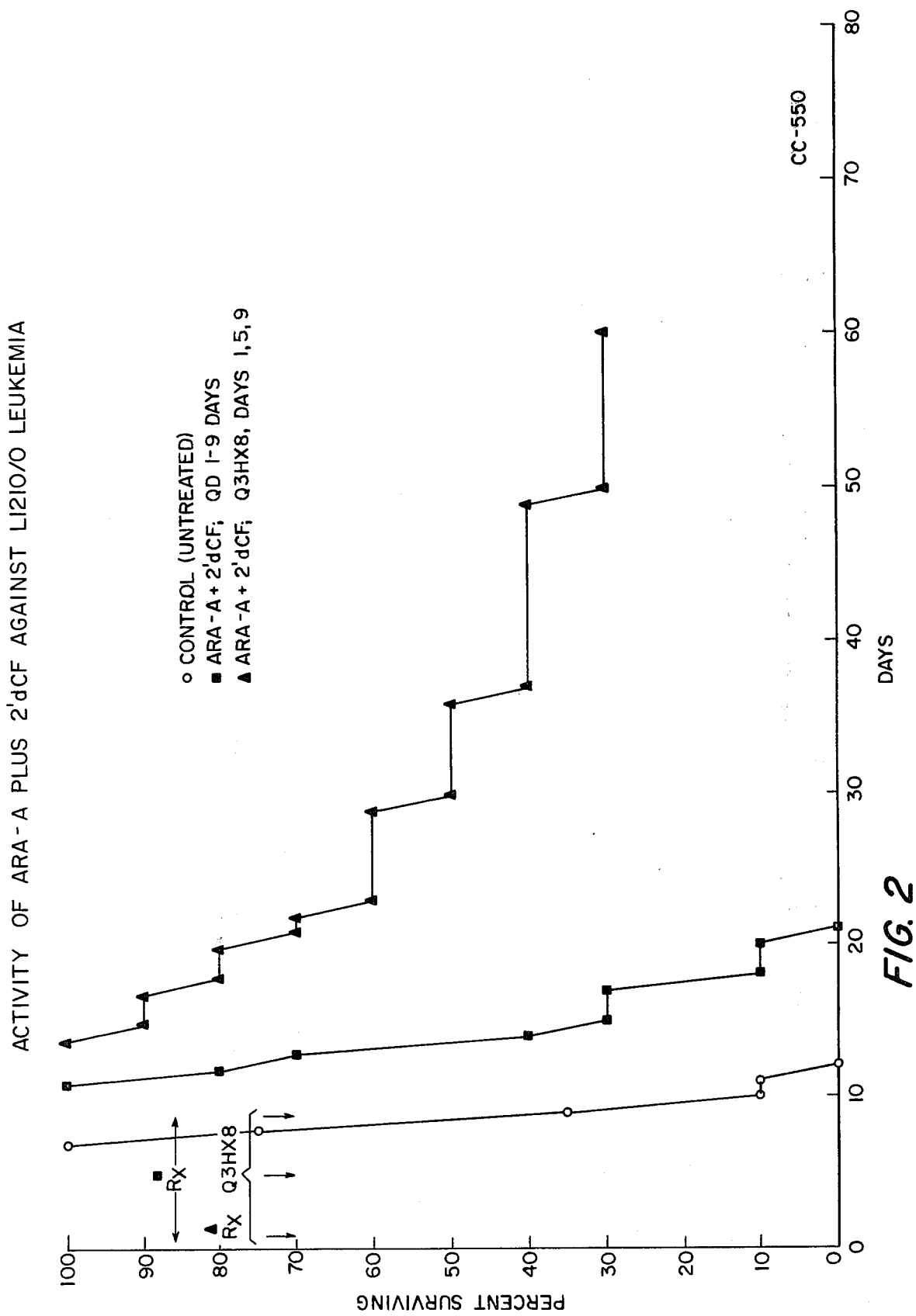
FIG. 2 shows the activity of ara-A plus 2'-dCF against L1210/0 leukemia as further explained in Table III.
Figure 3:
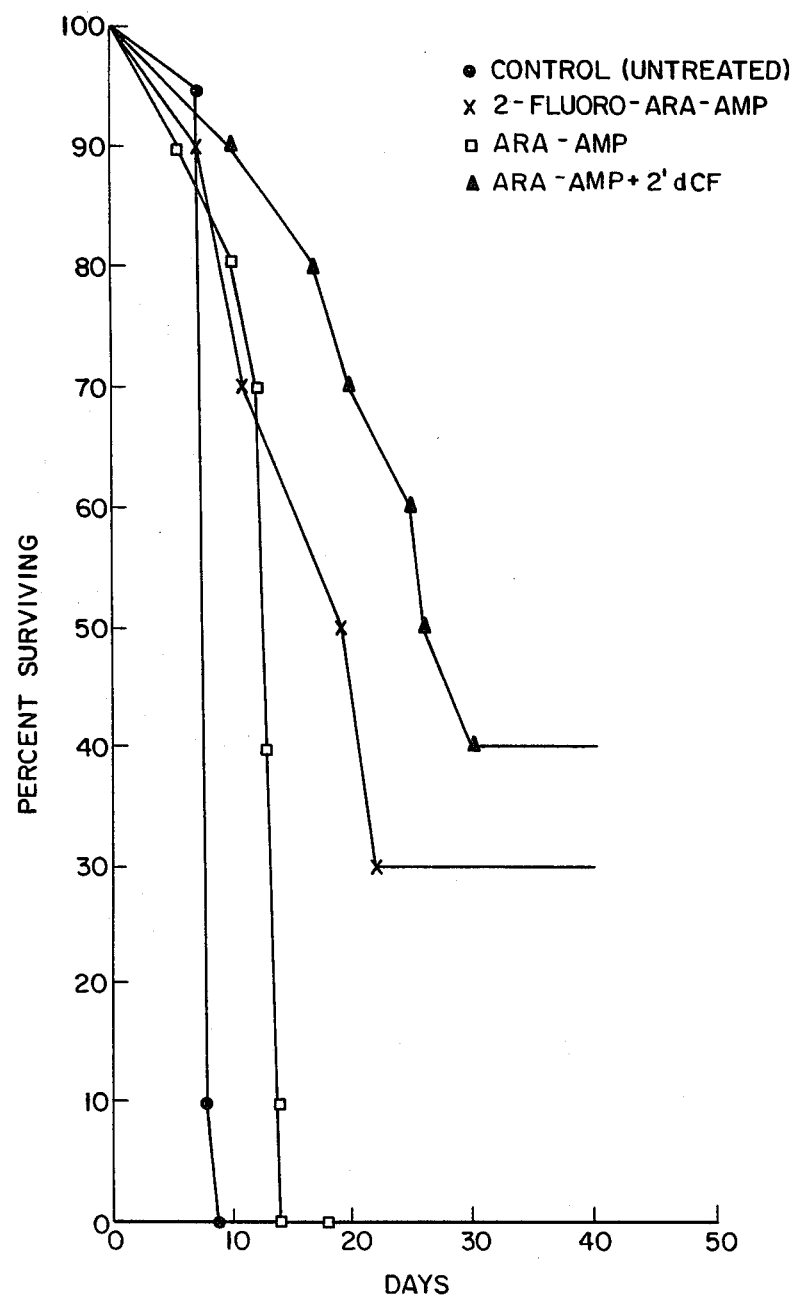
FIG. 3 shows the comparison of 2-fluoro-ara-AMP and 2'-dCF plus ara-A against L1210 leukemia $10^5$ L1210 cell IP as further explained in Table IV.

It has been noted that the antitumor activity of 9-β-D-arabinofuranosyl adenine (ara-A) is enhanced by the incorporation of a fluorine atom at the 2-carbon. This structural feature presents the enzymatic destruction of ara-A by the ubiquitous enzyme adenosine deaminase but does not interfere with phosphorylation of the molecule and destruction of leukemic cells by the resulting triphosphate of F-ara-A, however, it is very insoluble and difficult to administer properly. To overcome this difficulty two water-soluble derivatives, the 5'-formate and the 5'-phosphate, were prepared. These compounds provided higher levels of F-ara-A triphosphate in leukemic cells than F-ara-A itself and resulted in good increases in lifespan and some cures of mice implanted with leukemia L1210 cells (see FIGS. 1 and 3). The 5'-formyl derivative gave a 177% increase in lifespan and three cures.

EXAMPLE I 9-(5-O-formyl-β-D-arabinofuranosyl)-2-fluoroadenine

A solution of 9-β-D-arabinofuranosyl-2-fluoroadenine (3.3 g, 11.6 mmol) in 98% formic acid (17.5 ml) was allowed to stand at 4° for seven days before it was evaporated to dryness in vacuo without heat. Cold heptane was added to the residue and evaporated in vacuo twice followed by cold acetone. The white solid was extracted with hot acetone, and the acetone solution evaporated to dryness in vacuo; yield, 3.22 g. High-pressure liquid chromatography and pmr data showed this material to be a mixture of 9-(5-O-formyl-β-D-arabinofuranosyl)-2-fluoroadenine (65%), 9-(3,5-di-O-formyl-β-D-arabinofuranosyl-2-fluoroadenine (20%), 9-(2,5-di-O-formyl-β-D-arabinofuranosyl)-2-fluoroadenine (9%), and 9-β-D-arabinofuranosyl-2-fluoroadenine (6%). These compounds were separated by preparative high-pressure liquid chromatography using a $C_{18}$ column eluted with water: acetonitrile (17:3). 5'-Formate-pmr in S: 4:15 (m, H$_2$, H$_3'$, and H$_4'$), 4.4 (m, 2H$_5'$), 5.8 (broad, OH), 6.2 (d, J$_1'2'$, 4 Hz, H$_1'$), 7.8 (s, NH$_2$), 8.1 (s, H$_8$), 8.3 (s, H of CHO). 3', 5'-Diformate-pmr in S: 4.2 (m, H$_2'$ and H$_4'$), 5.4 (t, H$_3'$), 6.23 (d, J$_1'2'$, 4 Hz, H$_1'$), 7.85 (s, NH$_2$), 8.15 (s, H$_8$), 8.3 and 8.4 (2s, 2 CH$\underline{O}$).

EXAMPLE II

9-β-D-arabinofuranosyl-2-fluoroadenine 5'-phosphate (R=H$_2$PO$_3$—)

9-β-D-Arabinofuranosyl-2-fluoroadenine (2.6 g, 9.1 mmol) was added to 23 ml of triethylphosphate containing POCl$_3$ (4.6 g, 30 mmol) held at 0°, and the mixture was stirred for 3½ hours before it was poured into 200 ml of ice water. The pH of the solution was adjusted to 2 with 6 N NaOH before it was extracted with CHCl$_3$ (2×180 ml) and then slurried with charcoal (40 g) and Celite (20 g) for 20 min. The solids were removed by filtration and washed with water until free of acid. The product was extracted with a mixture of SOEtOH:NH$_2$OH:9H$_2$O. The basic solution was lyophilized to give the product 3.46 g.

Some of this material was converted to the free acid by means of a Domex 1×8 (formate form) column. UV$_{max}$ (e×10$^{-3}$): 262 (13.5), pH 7-262 (15.5), pH 13-261 (15.2).

Anal. Calcd. for C$_{10}$H$_{13}$FN$_5$O$_7$P.¾H$_2$O: C, 31.71; H, 3.86; N, 18.49. Found: C, 32.00; H, 3.86; N, 18.35.

We claim:

1. 9-(5-O-formyl-β-D-arabinofuranosyl)-2-fluoroadenine.

2. A method for treating L1210 cancer in mice by administration of an aqueous solution of an effective amount of an agent consisting of 5'-O-formyl derivative of O-β-D-arabinofuranosyl-2-fluoroadenine.

3. A method of treating mouse cancer according to claim 2 wherein an oral dosage is administered in an effective amount of a dosage of 10 to 250 mg/kg/day in a unitary regimen.

4. 9-(5-O-phosphate-β-D-arabinofuranosyl)-2-fluoroadenine.

5. A method of treating L1210 mouse cancer by administration of an aqueous solution of an effective amount of an agent consisting of 5-O-phosphate derivative of O-β-D-arabinofuranosyl-2-fluoroadenine.

6. A method of treating mouse cancer by administration of an effective amount of an aqueous solution of 5' phosphate of 9-β-D-arabinofuranosyl-2-fluoroadenine.

7. A method for treating L1210 cancer in mice wherein the 5' phosphate of 9-β-D-arabinofuranosyl-2-fluoroadenine is administered in an effective amount of a dosage of 10 to 250 mg.

* * * * *

UNITED STATES PATENT AND TRADEMARK OFFICE

CERTIFICATE EXTENDING PATENT TERM
UNDER 35 U.S.C. § 156

PATENT NO.:      4,357,324

DATED:           November 2, 1982

INVENTORS:       John A. Montgomery et al.

PATENT OWNER:    The United States of America as represented by the Secretary of the Department of Health and Human Services This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

2 YEARS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks